(12) United States Patent
Aebi et al.

(10) Patent No.: US 6,443,990 B1
(45) Date of Patent: Sep. 3, 2002

(54) ADJUSTABLE INTERVERTEBRAL IMPLANT

(75) Inventors: Max Aebi, Montreal (CA); Inga Knothe, Grenchen; Alfred Benoit, Lengnau, both of (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/664,731

(22) Filed: Sep. 19, 2000

Related U.S. Application Data

(63) Continuation of application No. 09/497,757, filed on Feb. 4, 2000, which is a continuation-in-part of application No. PCT/CH97/00293, filed on Aug. 6, 1997.

(51) Int. Cl.[7] .................................................. A61F 2/44
(52) U.S. Cl. ...................................... 623/17.16; 606/61
(58) Field of Search .......................... 623/17.16, 17.11, 623/17.15; 606/61

(56) References Cited

U.S. PATENT DOCUMENTS 5,370,697 A * 12/1994 Baumgartner ................ 623/17
5,554,191 A * 9/1996 Lahille et al. ................ 623/17
5,653,763 A * 8/1997 Errico et al. .................. 623/17
5,888,228 A * 3/1999 Knothe et al. ................ 623/17

FOREIGN PATENT DOCUMENTS

DE  44 16 605 C1  6/1995
EP  0 664 994 A1  1/1995

* cited by examiner

Primary Examiner—Corrine McDermott
Assistant Examiner—William H Matthews
(74) Attorney, Agent, or Firm—Pennie & Edmonds LLP

(57) ABSTRACT

An intervertebral implant in the form of a support unit with a central yoke and four legs extending in a direction is described. The legs are configured in two substantially mutually parallel planes spaced apart by the yoke and are abuttable as support surfaces against adjacent vertebrae. A guide cylinder extending from the yoke in the same direction as the legs has at least on threaded surface. A dilator member is adapted to be fixed to the guide cylinder and to deformably spread the legs of the intervertebral implant a predetermined amount. The gaps between the legs which the dilator member spreads may have grooves to arrest the dilator member in a predetermined location.

22 Claims, 4 Drawing Sheets

ADJUSTABLE INTERVERTEBRAL IMPLANT

This application is a continuation of copending U.S. application Ser. No. 09/497,757, filed Feb. 4, 2000, which is a continuation-in-part of the national stage entry of International Patent Application PCT/CH97/00293, filed Aug. 6, 1997, the entire contents of which is expressly incorporated herein by reference.

FIELD OF THE INVENTION

The invention relates to an adjustable intervertebral implant and expansion unit that allows continuous, as opposed to discrete, adjustment of the support of the spine.

BACKGROUND OF THE INVENTION

The bones and connective tissue of an adult human spinal column consists of more than twenty discrete bones coupled sequentially to one another by a tri-joint complex which consists of an anterior disc and the two posterior facet joints, the anterior discs of adjacent bones being cushioned by cartilage spacers referred to as intervertebral discs. The spinal column of bones is highly complex in that it includes the coupled bones, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes which can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

These prior art devices generally include a tubular metal body having an external surface threading. They are inserted transverse to the axis of the spine, into preformed cylindrical holes at the junction of adjacent vertebral bodies. Two cages are generally inserted side by side with the external threading tapping into the lower surface of the vertebral bone above, and the upper surface of the vertebral bone below. The cages include holes through which the adjacent bones are to grow. Additional material, for example autogenous bone graft materials, may be inserted into the hollow interior of the cage to incite or accelerate the growth of the bone into the cage.

These cages have enjoyed clinical success in promoting fusion and grossly approximating proper disc height, however, they do have specific drawbacks which limit their effectiveness. First among these drawbacks is that the devices, once implanted, do not permit the spine to retain its original and proper curvature. Causing a fusion to grow and immobilize the spine at a curvature which is not natural can cause discomfort and potentially damaging effects.

European Patent Application No 664,994 describes an intervertebral implant. The drawback of this device is that the implant is integral with the expander unit. This device can be inserted only as a unit into the intervertebral space, so that insertion must be by knocking the implant into its site. Moreover this intervertebral implant can be expanded only discretely, whereby the pre-surgical planning of the expansion angle can be carried out only inexactly.

SUMMARY OF THE INVENTION

An intervertebral implant for insertion into an intervertebral space between adjacent vertebrae is described. The intervertebral implant comprises a yoke member having an first surface facing in a first direction and a second surface facing in a second direction. There are four legs attached to the yoke member. These legs extend in the second direction. The legs are sized and shaped to support abutting vertebrae: the first and third legs being shaped and sized to support a first vertebrae, and second and fourth legs being shaped and sized to support a second vertebrae. The first and third legs define a first vertebral plane and the second and fourth legs define a second vertebral plane, and wherein the first vertebral plane and second vertebral plane are substantially mutually parallel. The ends remote from the yoke member of the four legs being spaced apart from one another. There is a first gap defined between the first and second legs and a second gap defined between the third and fourth legs. There is a guide cylinder attached to the yoke member and extending in the second direction. The guide cylinder has a threaded surface extending at least along a portion thereof.

In one embodiment the legs are integral with the yoke. The legs and the yoke form a U shape. The guide cylinder runs between the four legs. In a preferred embodiment, the guide cylinder is hollow, and the threaded portion is on the interior, the exterior, or most preferably on both the interior and the exterior of the hollow cylinder. The intervertebral implant may have one or more guide ribs extending from the side of the legs opposite the side facing the first gap or the second gap. These guide ribs typically run substantially parallel to the guide cylinder and/or form a herringbone or a serrate contour. The legs comprise perforations to facilitate bone growth through the intervertebral implant. The legs may have one or more lips that help keep bone chips, inserted to promote bone growth, in place between the legs.

The intervertebral implant further comprises a dilator member configured to simultaneously spread the first gap and the second gap as the dilator member travels along the guide cylinder toward the yoke member. The dilator member slidingly interacts with a portion of the legs facing the first and second gaps, thereby expanding the gap between the legs. One or more grooves are preferably placed in the portion of the legs facing the first gap, the second gap, or both, that is contacted by the dilator member. These grooves are shaped and sized so that a portion of the dilator member can enter the grooves. The grooves are a predetermined distance from the yoke. In its fixed position, the dilator member is threadably connected to the guide cylinder.

A tool useful for inserting the expansion unit is an insertion bush. The insertion bush is substantially cylindrical and has a hole running along the longitudinal axis. The hole is shaped and sized to permit the guide cylinder to slide into the hole. The outer diameter on at least a portion of the insertion bush is greater than the distance between the first intervertebral and second intervertebral planes. The insertion bush has a thread on an outer surface, where the thread is adapted to contact vertebrae.

BRIEF DESCRIPTION OF THE DRAWINGS

Several illustrative embodiments of the invention are shown in the figures.

DETAILED DESCRIPTION OF THE INVENTION

The invention is a continuously adjustable intervertebral implant in the form of a support unit comprising a central yoke and legs integral with said yoke. The legs are in two essentially mutually parallel planes on either side of the yoke, and are shaped and sized to be as support surfaces against adjacent vertebrae. The yoke includes a guide cylinder running essentially parallel to and between the legs and having at least one threaded portion. The threaded portion can be on the interior (an inside thread), or on the exterior (an outside thread), or both, of the guide cylinder. The guide cylinder, preferably a hollow cylinder at least at its end opposite to the yoke, is configured in a stable rotational position at the central yoke.

The invention is also a insertion and placement device to insert the intervertebral implant. The invention is also an atraumatic insertion procedure using the continuously adjustable intervertebral implant and the insertion device.

One embodiment of the invention is an intervertebral implant which, in a first stage of the insertion procedure, can be screwed or atraumaticly inserted into the intervertebral space. The intervertebral implant assembly can be expanded, in a second stage of the insertion procedure, using an expansion unit insertable into the intervertebral space. This expansion shall be continuous and allow monitoring, so that the expansion angle can be planned prior to surgery.

The invention will be further described with reference to the figures.

Figure 1:
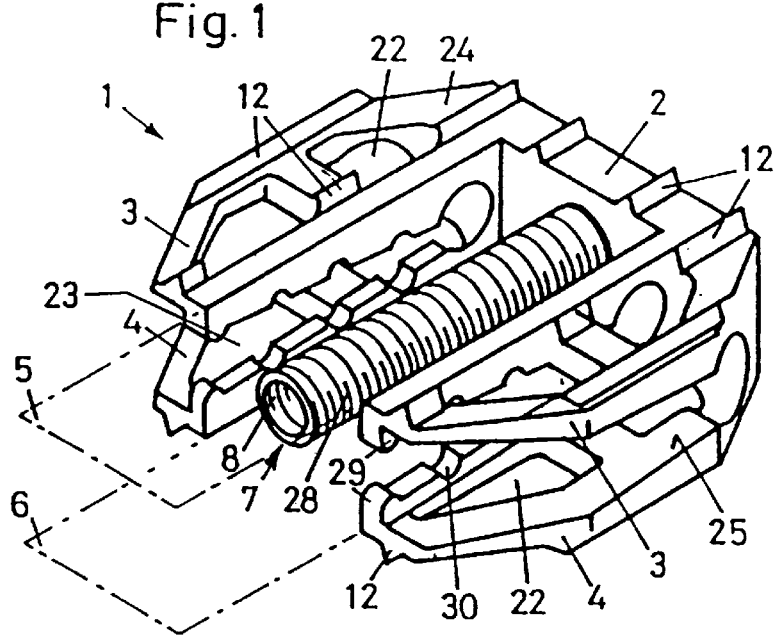
FIG. 1 is a perspective of the intervertebral implant of the invention.

An embodiment of the intervertebral implant shown in FIG. 1 assumes the shape of a support unit 1 comprising a central yoke 2, a guide cylinder 7, two upper legs 3, and two lower legs 4. The legs 3, 4 are integral with this yoke 2. Each of the legs 3, 4 is connected to the central yoke 2. In one embodiment, each of the legs 3, 4 is connected to the central yoke 2 on one end of the leg.

The top of the upper legs 3 and the bottom of the lower legs 4 are configured in two substantially mutually parallel planes 5, 6 spaced apart by the yoke 2 relative to which they are substantially symmetrical. The planes 5, 6 are abuttable to and may represent the support surfaces against adjacent vertebrae.

A pair consisting of one upper leg 3 and one lower leg 4 are connected to each of the two sides of the yoke. There is a gap 23 between each of the two pairs of legs 3, 4. In the embodiment of FIG. 1, a portion of the gap defined by the sides of the legs facing the upper legs 3 and lower legs 4, increases substantially continuously with distance from the yoke 2. By substantially continuous, it is meant that the a portion of the gap 23 increases in width with increasing distance from the yoke 2, not including areas of the gap 23 where grooves 30 or lips 29 are present, and not including an area of the gap 23 near the yoke 2 where the gap 23 is expanded to increase the flexibility of the yoke 2 or of the legs 3, 4 to facilitate support unit 1 deformation and expansion.

The guide cylinder 7 extends perpendicularly from the center of the yoke 2. The guide cylinder 7 is preferably hollow, thereby having an inner wall and an outer wall. The hollow guide cylinder 7 is fitted in a preferred embodiment with an inside thread 8 and an outside thread 28 and is situated between and essentially parallel to the legs 3, 4. A portion of the inside surfaces 25 of the legs 3, 4 are fitted with grooves 30 running transversely to the guide cylinder 7. The location of the grooves 30 from the yoke 2 may be preselected. The outside surfaces 24 of the legs 3, 4 are beneficially fitted with guide ribs 12 running substantially parallel to the guide cylinder 7 to facilitate insertion and stability. In preferred embodiments, the guide ribs 12 follow a herringbone or a serrate contour. Moreover the legs 3, 4 may have perforations 22 and an inward-pointing lip 29 at their free front ends. The perforations 22 encourage bone growth into and between the legs. For the same purpose, the legs and the yoke form a U-shaped support unit, the legs being affixed to the ends of the yoke, and hence a free space being subtended in each plane between the two legs to allow bone growth into it. The inward-pointing lips 29 prevent the bone chips filled into the implant 1, also for the purpose of encouraging bone growth, from slipping out.

A pair of legs 3, 4 is present in each plane 5, 6 of the U-shaped support unit 1. The legs 3, 4 and the yoke 2 to subtend the gap 23 (shown with bone chips contained therein in FIG. 8) in each plane 5, 6.

Figure 2:
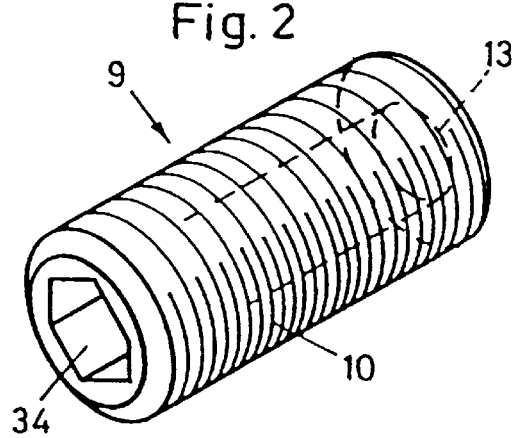
FIG. 2 is a perspective of a threaded insertion bush for use with the intervertebral implant of FIG. 1.

FIG. 2 shows a bush 9 with an outer thread 10, a cavity 13 and a hexagonal socket 34. The selection of a hexagonal socket is for convenience, and any configuration that provides a grip where the bush 9 can be rotated can be used. The bush 9 is slippable onto the guide cylinder 7 of the support unit 1. While the bush diameter can be of any workable size, a preferred size is when the diameter of the bush 9 is slightly larger than the height of the support unit 1, that is, slightly larger than the spacing between planes 5 and 6.

The bush 9 inserted into the support unit 1 can be rotated about the guide cylinder 7 using an appropriate instrument inserted into the hexagonal socket 34 and is used to insert the support unit 1 into the intervertebral space. Because the bush 9 slightly projects beyond the outsides 24 of the legs 3, 4, part of its outer thread 10 engages the bone material of the adjacent vertebra, and thereby the support unit 1 is easily slipped or rotated into the intervertebral space. Once the support 1 has been inserted into the intervertebral space, the bush 9 also is easily screwed out of the intervertebral space and away from the guide cylinder 7.

Figure 4:
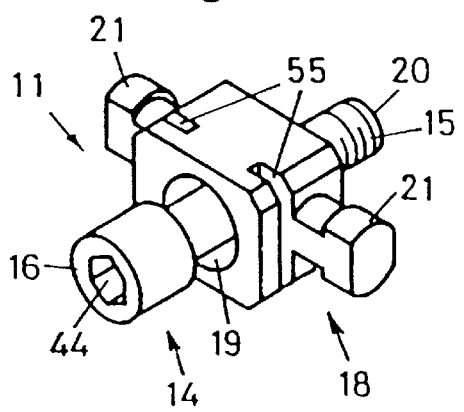
FIG. 4 is a perspective of a modified expansion unit with screw for use with the intervertebral implant of FIG. 1.
Figure 3:
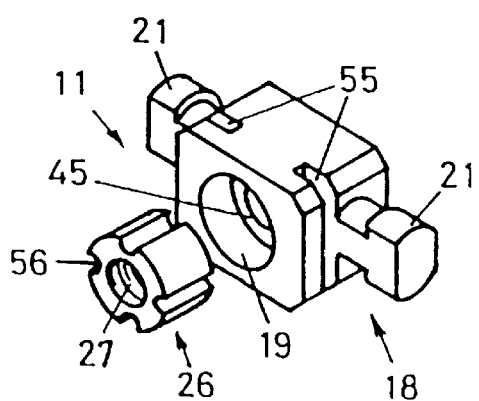
FIG. 3 is a perspective of an expansion unit with nut for the intervertebral implant of FIG. 1.

FIGS. 3 and 4 show two embodiments of an expansion unit 11 used for expanding the support unit 1. Each embodiment comprises a dilator element 18. The dilator element 18 body beneficially assumes the shape of a right parallelepiped having a central borehole 19 and is fitted with two side cams 21, one on each of opposing ends of the dilator element 18. The dilator element 18 is insertable between the legs 3, 4 of the support unit 1. The side cams 21 on the dilator element 18 slidably interact with the upper legs 3 and the lower legs 4 to spread apart the upper legs 3 from the lower legs 4. Advantageously, an expanded section on the end of each side cam 21 beneficially interact with the upper legs 3 and the lower legs 4 to keep the side cams 21 positioned in the gap between the upper legs 3 and the lower legs 4. The size of the side cams 21 are such that the side cams 21 can partially enter the grooves 30. This advantageously may be used to provide an indicator that the expansion unit 11 is in the correct location and the support unit 1 is expanded the correct amount, and also increased resistance to movement along the guide cylinder 7 may help hold the dilator element 18 in location. The side cams 21 advantageously comprises two lateral slots 55 to seize and handle the side cams 21.

The embodiment of the expansion unit 11 shown in FIG. 3 comprises a hollow, preferably cylindrical nut 26 with an inside thread 27 matching the outside thread 28 of the guide cylinder 7. The geometry of the borehole 19 is such that the nut 26 can enter the borehole until the nut 26 abuts the stop 45.

The embodiment of the expansion unit 11 is shown in FIG. 4 comprises a screw 14 with a head 16 fitted with a hexagonal socket 44 and a shank 20. The shank 20 is fitted with an outer thread 15 that matches the inner thread 8 of the guide cylinder 7. Similar to the case of the nut 26 of FIG. 3, the head 16 of the screw 14 can enter the borehole until the head 16 abuts the stop 45 within the central borehole 19.

Figure 12:
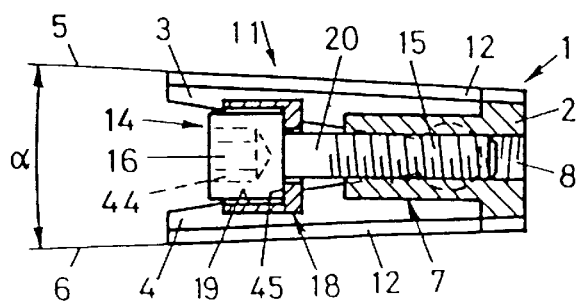
FIG. 12 is a longitudinal section of a modified intervertebral implant of the invention having a shortened guide cylinder and an expansion unit of FIG. 4 screwed into

When using the second embodiment variation of the expansion unit 11 shown in FIG. 4, the guide cylinder 7 is shortened in the manner shown in FIG. 12, that is, it is approximately half the length of that shown in FIG. 1.

The method of insertion and expansion of intervertebral implant of the invention is discussed in further detail below in relation to FIGS. 5 through 13.

Figure 5:
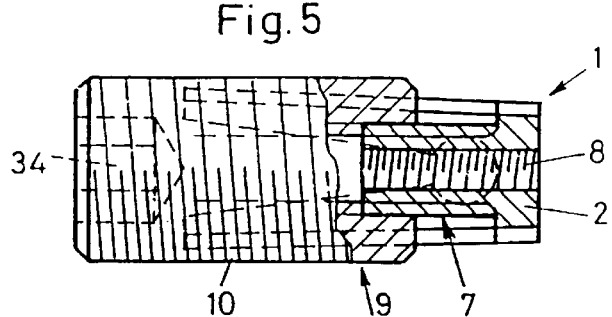
FIG. 5 is a perspective of a section of the expansion unit showing the insertion of the threaded bush.

Upon removal of enough intervertebral-disk material, the U-shaped support unit 1 is inserted between the affected vertebrae. To place the support unit 1 in its correct position between the vertebrae, and as shown in FIG. 5, the bush 9 fitted with outer thread 10 is slipped over the guide cylinder 7 of said support unit 1. The U-shaped support unit 1 together with the slipped-on bush 9 is lightly forced into the prepared intervertebral space until the first turn of the outer thread 10 on the bush 9 engages the bone material. Thereafter, by further rotating the bush 9, the U-shaped support unit 1 is screwed to the desired depth into the intervertebral space. The rotation of the bush 9 may be implemented by a tool inserted into the hexagonal socket 34.

Figure 6:
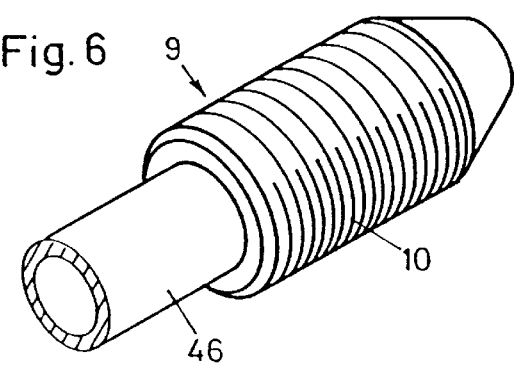
FIG. 6 is a perspective of a modified threaded bush with a hollow, cylindrical shank.
Figure 7:
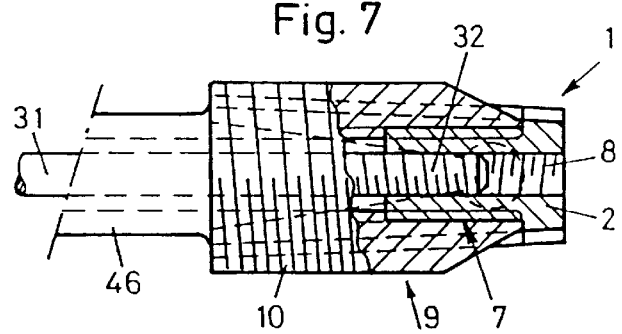
FIG. 7 is a perspective of a section of the intervertebral implant with the bush of FIG. 6 in the inserted position.

In a variation shown in FIGS. 6 and 7, the bush 9 fitted with the outer thread 10 is affixed to a hollow, cylindrical shank 46 and forms a part of an insertion implement. For better guidance of the insertion implement, a guide spindle 31 shown in FIG. 7 is fitted at its front end with an outer thread 32 (shown in FIG. 10). This guide spindle 31 can be previously screwed into the inside thread 8 of the guide cylinder 7 of the support unit 1 and can remain there during the full time of surgery. The bush 9 then can be easily slipped by its hollow, cylindrical shank 46 over the guide spindle 31 onto the guide cylinder 7 and be rotated when on latter.

The guide ribs 12 present on the outer sides 24 of the legs 3, 4 of the support unit 1 help prevent said support unit 1 from deviating off the desired direction during the insertion procedure.

Following insertion of the bush and placement of the support unit, the bush 9 is screwed out of the intervertebral space and away from the support unit 1. Advantageously, practically no friction will be present between the guide cylinder 7 and the inside surface of the bush 9. The support unit 1 therefore remains in place while the bush 9 is withdrawn.

Figure 8:
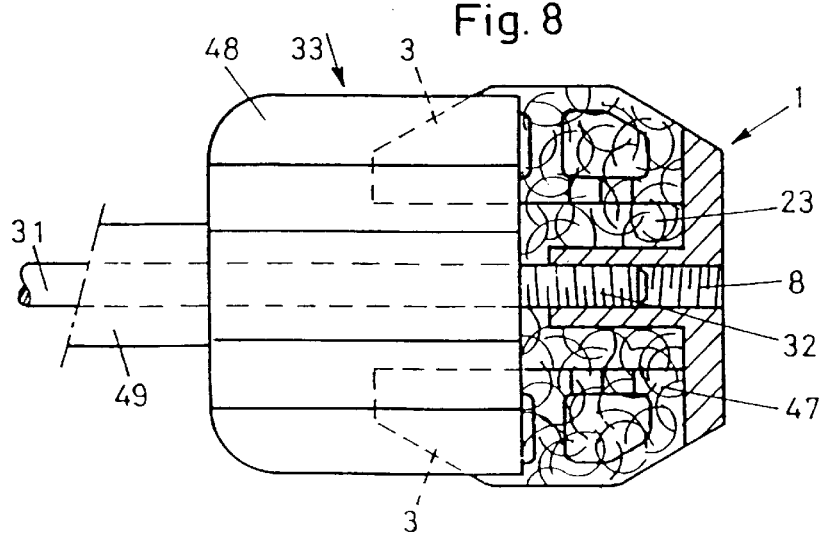
FIG. 8 is a perspective of a section of an intervertebral implant of the invention with a partly inserted bone-chip impactor.
Figure 9:
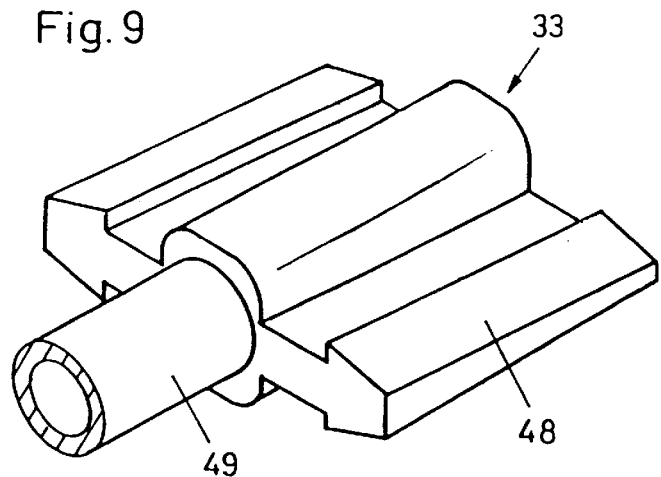
FIG. 9 is a partial perspective of the bone-chip impactor of FIG. 8.

Optionally, and as shown in FIG. 8, bone chips or another osteogenetic, that is, osteoinductive or osteoconductive material 47 may be introduced into the free space 23 of the support unit 1. A bone-chip impactor 33, shown in FIG. 8, can be used to introduce and compress bone chips 47 into the free space 23. The bone-chip impactor 33 consists of a flat or contoured base 48 which, as shown in FIG. 8, can be partly inserted between the legs 3, 4. The bone-chip impactor 33 is affixed to a hollow, cylindrical shank 49. The bone-chip impactor 33 can be axially guided on the guide spindle 31.

Figure 10:
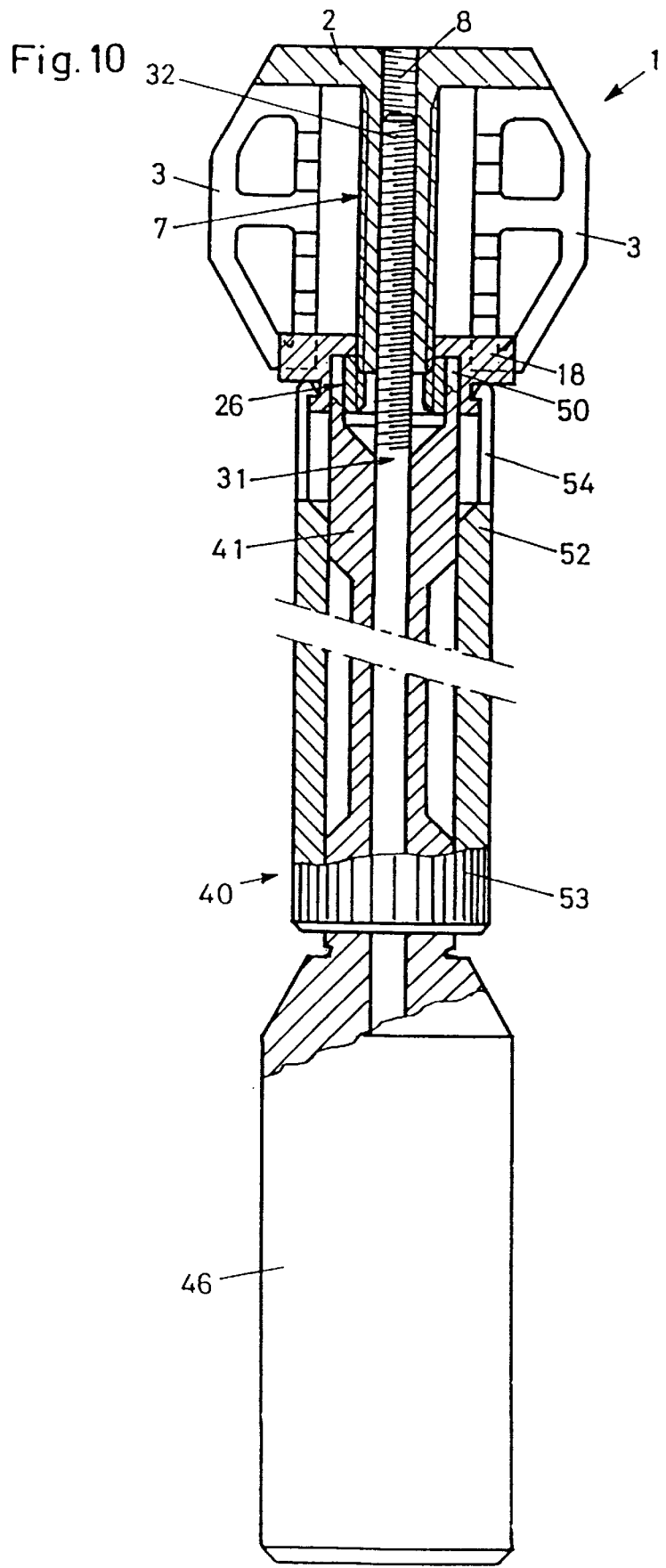
FIG. 10 is a cross-section of an intervertebral implant of FIG. 1 with an inserted expansion unit of FIG. 3 being screwed by an insertion instrument slipped over the guide spindle into the support unit.

Lastly, as shown in FIG. 10, the expansion unit 11 is introduced between the planes 5, 6 and legs 3, 4 of the support unit 1. Then, the expansion unit 11 of FIG. 3 is inserted in its assembled state, that is, with the nut 26 inserted into the borehole 19, by means of the insertion implement 40 such that its dilator element 18 and two cams 21 are between the legs 3, 4. The portion of the side cams 21 that extend between the upper legs 3 and the lower legs 4 are at some point larger than the gap. The side cams 21 then slidably interact with and spread the upper legs 3 from the lower legs 4.

Figure 11:
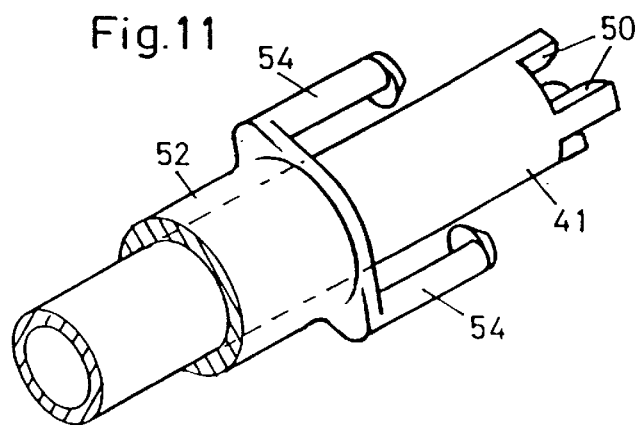
FIG. 11 is a partial perspective of the insertion instrument shown in FIG. 10.

The front end of one embodiment of the insertion implement 40 is shown in detail in FIG. 11. At its front end, that is, the end facing the intervertebral space, the rotatable insertion implement bush 41 comprises four drive cams 50, where the drive cams 50 are of a size and placement so as to be able to operatively engage the nut 26. Four matching longitudinal grooves 56 are present for that purpose in the nut 26 to facilitate its rotation. The rotatable insertion implement bush 41 is supported inside the holding stub 52, wherein said holding stub 52 advantageously has a knurled ring 53 (shown in FIG. 10) and is fitted at its front end with two holding pins 54 insertable into the lateral slots 55 (shown in FIG. 3) of the cams 21 in order to hold the dilator element 18.

Figure 13:
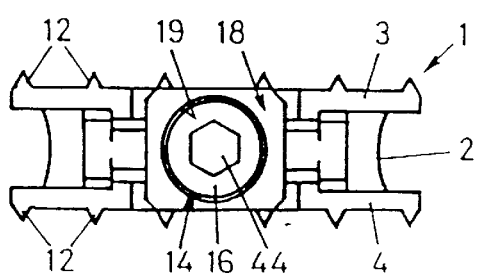
FIG. 13 is a front view of the intervertebral implant of FIG. 12 with screwed-in expansion unit.

When using an expansion unit 11 as shown in FIG. 4, which in addition to the identical dilator element 18 comprises a screw 14 (in lieu of the nut 26), the screw 14 engages an inside thread 8 on the guide cylinder 7. The shank 20 of the screw 14 has a thread 15 that matches the inside thread 8 of the hollow guide cylinder 7. The screw 14 is inserted by its thread 15 into the inside thread 8 of the hollow guide cylinder 7 (FIGS. 12 and 13). By screwing the screw 14 into the guide cylinder 7, the action of the screw head 16 against the stop 45 in the borehole 19 will cause axial displacement of the dilator element 18 toward the guide cylinder 7.

The cams 21 affixed to the expansion element 18 enter the space between the legs 3, 4 and spread apart the legs, thereby expanding the support unit 1. By a further inward rotation of the screw 14 or the nut 26, the legs 3, 4 can be spread apart so much that for some embodiments their planes 5, 6 subtend an angle α of about 0 to about 20 degrees, more typically about 10 to about 12 degrees from parallel. Said inward rotation of the screw 14 can be carried out using a tool inserted into the hexagonal socket 44 in the head 16.

The guide cylinder 7 is fitted with either a thread on the inside of the hollow cylinder, called herein an inside thread 8, or a thread on the outside of the guide cylinder, called herein an outside or outer thread 28, or with both. The inside thread 8 allows expanding the implant 1 using an expansion unit 11 that is shown in FIG. 3 with a spindle 31 fitted with a spindle thread matching the said inside thread 8. The guide cylinder outside thread 28 simultaneously allows expanding the implant 1 when using a expansion unit 11 fitted with a hollow-cylinder segment, i.e., a nut 26, having a thread 27 matching the outer thread 8. Because of the larger diameter, the latter variation allows transmitting higher tensile forces.

The embodiment of the guide cylinder 7 fitted with both an inside 8 and an outside thread 28 offers the additional advantage that other aspects of surgery can be carried out in guided manner. A guide spindle 31 affixed in the inside thread and over which the other instruments may be displaced can be used as an accessory guide element during all of surgery.

Essentially typical surgery takes place in three stages: inserting the implant 1 in a controlled manner using a threaded case or bush 9 to push the implant 1 into the desired location; filling the implant 1 with bone chips and optionally compacting the chips with a bone-chip impactor 33; and inserting an expansion unit 11 comprising a dilator member 18 threadably attached to the guide cylinder 7 to the predetermined location, thereby expanding the implant 1 in the intervertebral space. An additional stage is conceivable, namely to inject bone-growth stimulating materials in liquid form or as gel into the intervertebral space. Perforated screw-in, or bone-chipping, insertion instruments may be used for such a purpose.

Some of the advantages of the invention are:
the patient s natural lordotic spine radius can be restored to the patient and this angle can be determined before surgery, and as a result optimal conditions for the ingrowth of the implant are present;
there is significant porosity and perforations available to enhance bone growth, and as a result optimal conditions for the ingrowth of the implant are present;
an atraumatic insertion procedure is made possible, namely the implant, instead of being knocked into position, can be screwed-in gently and in monitored manner; and
simplified and minimally invasive surgery is henceforth feasible, that is, a three-stage surgical technique being controlled by means of a guide spindle.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

We claim:
1. An intervertebral implant for insertion into an intervertebral space between adjacent vertebrae, the intervertebral implant comprising:
   a yoke member having an first surface facing in a first direction and a second surface facing in a second direction;
   four legs attached to the yoke member and extending in the second direction, the ends remote from the yoke member of the four legs being spaced apart from one another, wherein there is a first gap defined between first and second legs and a second gap defined between third and fourth legs;
   a guide cylinder attached to the yoke member and extending in the second direction, the guide cylinder having a threaded surface extending at least along a portion thereof, wherein the legs being sized and shaped to support abutting vertebrae, the first and third legs being shaped and sized to support a first vertebrae, and second and fourth legs being shaped and sized to support a second vertebrae;
   a dilator member configured to simultaneously spread the first gap and the second gap as the dilator member travels along the guide cylinder toward the yoke member; and
   a first groove in the first leg on the portion of the first leg facing the first gap that is contacted by the dilator member, wherein the first groove runs transverse to the guide cylinder, wherein the first groove is shaped and sized so that a portion of the dilator member can enter the first groove, and wherein the first groove is a predetermined distance from the yoke.
2. The intervertebral implant of claim 1 wherein the legs are integral with the yoke, wherein the first and third legs define a first vertebral plane and the second and fourth legs define a second vertebral plane, wherein the first vertebral plane and second vertebral plane are substantially mutually parallel, and wherein the guide cylinder is rotationally stable with respect to the yoke.
3. The intervertebral implant of claim 1 wherein the first leg and the second leg and the yoke form a U shape, and wherein the guide cylinder runs between the four legs.
4. The intervertebral implant of claim 1 wherein the guide cylinder is hollow, and the threaded portion is on the interior or the exterior of the hollow cylinder.
5. The intervertebral implant of claim 1 wherein the guide cylinder is hollow, and the threaded portion is on both the interior and the exterior of the hollow cylinder.
6. The intervertebral implant of claim 1 further comprising a guide rib extending from the side of the legs opposite the side facing the first gap or the second gap, wherein the guide rib runs substantially parallel to the guide cylinder.
7. The intervertebral implant of claim 1 further comprising guide ribs extending from the sides of the legs opposite the sides facing the first gap and the second gap, wherein the guide ribs form a herringbone or a serrate contour.
8. The intervertebral implant of claim 1 wherein the legs comprise perforations.
9. The intervertebral implant of claim 1 further comprising a first lip on the end of the first leg remote from the yoke, the first lip extending toward the third leg, and a second lip on the end of the second leg remote from the yoke, the second lip extending toward the fourth leg.
10. The intervertebral implant of claim 1 wherein the dilator member slidingly interacts with a portion of the legs facing the first and second gaps, and wherein the distance between the portion of the legs facing the first and second gaps contacted by the dilator member increase substantially continuously with distance from the yoke.

11. The intervertebral implant of claim 1 further comprising a second groove in the third leg on the portion of the third leg facing the second gap that is contacted by the dilator member, wherein the second groove runs transverse to the guide cylinder, wherein the second groove is shaped and sized so that a portion of the dilator member can enter the second groove, and wherein the second groove is a predetermined distance from the yoke.

12. The intervertebral implant of claim 1 wherein the dilator member is threadably connected to the guide cylinder.

13. The intervertebral implant of claim 1 wherein the dilator member comprises a body and side cams disposed on opposing ends of the dilator body, wherein the side cams are shaped and sized to slidably interact with the legs to spread the first and second gaps.

14. The intervertebral implant of claim 13 further comprising a nut with an inner thread adapted to match an outer thread of the guide cylinder and adapted to prevent the dilator member from sliding in at least one direction along the guide cylinder, wherein the dilator member body has a hole adapted to permit the guide cylinder to slidably enter the hole, and wherein the guide cylinder comprises a thread on the outer surface of the cylinder.

15. The intervertebral implant of claim 13 further comprises a bolt with an outer thread adapted to match an inner thread of the guide cylinder and adapted to prevent the dilator member from sliding in at least one direction along the guide cylinder, wherein the dilator member body has a hole adapted to permit the bolt to slidably enter the hole, and wherein the guide cylinder comprises a hollow cylinder with a thread on at least a portion of the inner surface of the hollow cylinder.

16. The intervertebral implant of claim 2 further comprising an insertion bush, wherein said insertion bush is substantially cylindrical, comprises a hole running at least partially along the longitudinal axis of the insertion bush, wherein said hole is shaped and sized to permit the guide cylinder to slide into the hole.

17. The intervertebral implant of claim 16 wherein the outer diameter on at least a portion of the insertion bush is greater than the distance between the first intervertebral and second intervertebral planes, and wherein the insertion bush comprises a thread on an outer surface.

18. The intervertebral implant of claim 1 further comprising a guide spindle with a spindle thread on at least a portion of the outer surface, wherein said spindle thread is affixable in the thread of the guide cylinder, wherein said guide spindle extends in the second direction to a distance further from the yoke than the legs.

19. An intervertebral implant for insertion into an intervertebral space between adjacent vertebrae, the intervertebral implant comprising:

a yoke member having an first surface facing in a first direction and a second surface facing in a second direction;

four legs attached to the yoke member and extending in the second direction, the ends remote from the yoke member of the four legs being spaced apart from one another, wherein there is a first gap defined between first and second legs and a second gap defined between third and fourth legs, wherein the legs are integral with the yoke, wherein the first and third legs define a first vertebral plane and the second and fourth legs define a second vertebral plane, wherein the first vertebral plane and second vertebral plane are substantially mutually parallel, wherein the guide cylinder is rotationally stable with respect to the yoke;

a guide cylinder attached to the yoke member and extending in the second direction, the guide cylinder having a threaded surface extending at least along a portion thereof, wherein the legs being sized and shaped to support abutting vertebrae, the first and third legs being shaped and sized to support a first vertebrae, and second and fourth legs being shaped and sized to support a second vertebrae; and an insertion bush, wherein said insertion bush is substantially cylindrical and comprises a hole running at least partially along the longitudinal axis of the insertion bush, wherein said hole is shaped and sized to permit the guide cylinder to slide into the hole.

20. The intervertebral implant of claim 19 wherein the outer diameter on at least a portion of the insertion bush is greater than the distance between the first intervertebral and second intervertebral planes, and wherein the insertion bush comprises a thread on an outer surface.

21. An intervertebral implant for insertion into an intervertebral space between adjacent vertebrae, the intervertebral implant comprising:

a yoke member having an first surface facing in a first direction and a second surface facing in a second direction;

four legs attached to the yoke member and extending in the second direction, the ends remote from the yoke member of the four legs being spaced apart from one another, wherein there is a first gap defined between first and second legs and a second gap defined between third and fourth legs;

a guide cylinder attached to the yoke member and extending in the second direction, the guide cylinder having a threaded surface extending at least along a portion thereof, wherein the legs being sized and shaped to support abutting vertebrae, the first and third legs being shaped and sized to support a first vertebrae, and second and fourth legs being shaped and sized to support a second vertebrae; and a guide spindle with a spindle thread on at least a portion of the outer surface, wherein said spindle thread is affixable in the thread of the guide cylinder, wherein said guide spindle extends in the second direction to a distance further from the yoke than the legs.

22. The intervertebral implant of claim 21 wherein the legs are integral with the yoke, wherein the first and third legs define a first vertebral plane and the second and fourth legs define a second vertebral plane, wherein the first vertebral plane and second vertebral plane are substantially mutually parallel, and wherein the guide cylinder is rotationally stable with respect to the yoke.

* * * * *